United States Patent [19]

Hattori et al.

[11] Patent Number: 5,672,782
[45] Date of Patent: Sep. 30, 1997

[54] PROCESS FOR PRODUCING TERTIARY ALCOHOL AND FOR PREPARING CATALYST THEREFOR

[75] Inventors: Akitaka Hattori; Kazuhiro Nakamura; Tomohiro Washiyama, all of Mie-ken; Takao Kato, Chiba-ken; Toshihiro Saito, Tokyo; Shoji Arai, Mie-ken, all of Japan

[73] Assignee: Tosoh Corporation, Yamaguchi-ken, Japan

[21] Appl. No.: 291,022

[22] Filed: Aug. 16, 1994

Related U.S. Application Data

[63] Continuation of Ser. No. 86,890, Jul. 7, 1993, abandoned.

[30] Foreign Application Priority Data

Jul. 13, 1992 [JP] Japan .................................. 4-206953
Dec. 14, 1992 [JP] Japan .................................. 4-332961

[51] Int. Cl.$^6$ ................................................ C07C 29/04
[52] U.S. Cl. .................................................. 568/899
[58] Field of Search ......................................... 568/899

[56] References Cited

U.S. PATENT DOCUMENTS

| | | | |
|---|---|---|---|
| 4,080,391 | 3/1978 | Tsumura et al. | 260/641 |
| 4,087,471 | 5/1978 | Bowman et al. | 568/899 |
| 4,340,769 | 7/1982 | Brandes et al. | 568/899 |
| 4,595,786 | 6/1986 | Waller | 568/835 |
| 4,956,506 | 9/1990 | Latimer | 568/899 |
| 5,094,995 | 3/1992 | Butt et al. | 502/402 |
| 5,233,102 | 8/1993 | Butt et al. | |

FOREIGN PATENT DOCUMENTS

| | | |
|---|---|---|
| 0 123 713 | 11/1984 | European Pat. Off. . |
| 0 415 310 A2 | 3/1991 | European Pat. Off. . |
| 0 415 310 A3 | 3/1991 | European Pat. Off. . |
| 2 340 330 | 9/1977 | France . |
| 2 054 568 | 2/1981 | United Kingdom . |

*Primary Examiner*—José G. Dees
*Assistant Examiner*—Samuel Barts
*Attorney, Agent, or Firm*—Nixon & Vanderhye

[57] ABSTRACT

A process for producing a polymer having sulfonic acid groups is provided which comprises treating a polymer having sulfonate salt groups with a ion-exchange resin to change the sulfonate salt groups into sulfonate acid groups with porous-type strongly acidic cation exchange resin. A process for producing a tertiary alcohol is also provided which comprises hydration of olefin by use of the aforementioned polymer as the catalyst. By the process, a tertiary alcohol is produced by hydration of olefin with high selectivity at low cost.

7 Claims, 1 Drawing Sheet

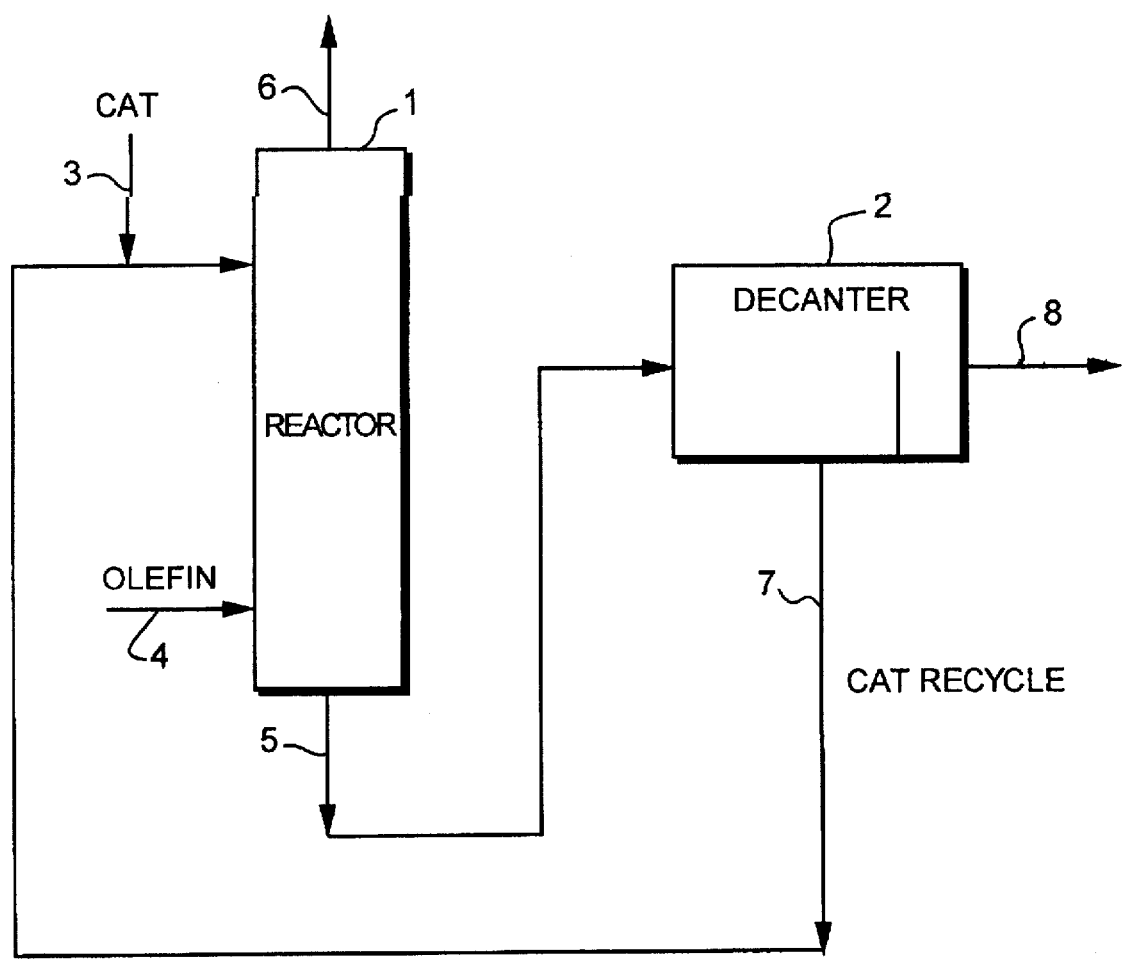

5,672,782

PROCESS FOR PRODUCING TERTIARY ALCOHOL AND FOR PREPARING CATALYST THEREFOR

This is a continuation of application Ser. No. 08/086,890, filed Jul. 7, 1993, now abandoned.

BACKGROUND OF THE INVENTION:

1. Field of the Invention:

The present invention relates to a process for producing a polymer having sulfonic acid groups which is soluble in water and/or an olefin, such as polystyrenesulfonic acid, through ion exchange of a polymer-sulfonate salt by use of a porous-type strongly acidic cation exchange resin.

The present invention also relates to a process for producing a tertiary alcohol industrially by employing the polymer having sulfonic acid groups as the catalyst.

Tertiary alcohols are useful not only as an industrial chemicals and solvent but also as a starting material for various industrial products. For example, tertiary butyl alcohol is consumed in a large amount as a starting material for methyl t-butyl either and methyl methacrylate.

2. Description of the Related Art:

Tertiary alcohols are produced conventionally by catalytic hydration of olefin. The conventional processes therefor are practiced usually in a liquid phase, and are classified into two types: heterogeneous catalytic processes which employ a solid catalyst, and homogeneous catalytic processes which employ an aqueous acidic catalyst solution.

A known heterogeneous catalytic process employs strongly acidic ion exchange resin as the catalyst (See, Japanese Patent Publication Sho-56-22855). In this process, the catalyst is an insoluble solid resin, and the olefin and water as the substrates are immiscible, so that the catalyst exhibits low activity because of insufficiency of the contact. For improvement thereof, a large amount of an organic acid such as acetic acid is added to the liquid reaction system to make the liquid phase homogeneous and to accelerate the hydration. In this improved process, the produced tertiary alcohol tends to change into an organic acid ester by reaction with the organic acid in the presence of the strongly acidic ion-exchange resin, which necessitates additionally an ester separation-recovery step and makes inevitably the process complicated. Further, this process is usually practiced by suspending the ion exchange resin through a batch process, whereby the olefin hydration reaction reaches chemical equilibrium, not giving satisfactorily high conversion of the olefin.

On the contrary, homogeneous catalytic processes employ, as the catalyst, sulfuric acid, heteropolyacid (Japanese Patent Publication No. Sho-58-39806), p-toluenesulfonic acid (Japanese Patent Publication No. Sho-62-12208), and the like. These homogeneous catalyst, which have high catalytic activity, form a homogeneous phase with the reaction products, and requires a step of separating the resulting tertiary alcohol from the aqueous catalyst solution. Usually, the tertiary alcohol is separated and recovered by distillation, which causes a reverse reaction or formation of a by-product, resulting in a low yield.

Therefore, separation method other than distillation is proposed for separating the produced tertiary alcohol from the catalyst in the homogeneous catalytic process. Japanese Patent Publication No. Sho-58-39806, for example, discloses a process in which a heteropolyacid is employed as the catalyst, an olefin containing a hydrocarbon inert to the hydration reaction is used as the starting material, and a large amount of tertiary alcohol or a specific inorganic salt is added to the reaction system to separate an organic phase containing the formed tertiary alcohol and an aqueous phase containing the catalyst. This process requires the use of an olefin containing a hydrocarbon inert to the hydration reaction and the preliminary addition of a large amount of tertiary alcohol to the reaction system. The requirements case limitation on the starting olefin and the addition of a large amount of tertiary alcohol disadvantageously cause decrease of the reaction velocity owing to the reverse reaction and require recycle of a large amount of the tertiary alcohol. Furthermore, the use of specific inorganic salt complicates the reaction system and give rise to a problem of corrosion.

On the other hand, the polymer having sulfonic acid groups is conventionally derived from a polymer having sulfonate salt groups by ion exchange. The polymer, however, is not brought into sufficient contact with the ion exchange resin because of low diffusibility of the high-molecular-weight polymer, and the ion exchange does not proceed rapidly. For example, Japanese Patent Application Laid-Open No. Sho-60-15408 discloses use of a porous-type cation exchange resin (Amberlite IR-120B) having crosslinking degree of 2 to 20%. In Example of this prior art, the ion exchange process requires a long time, and a large amount of the ion exchange resin has to be used, which requires high cost. Moreover, in this method, a polymer cannot readily be obtained which exhibits high exchange ratio of the metallic cation in the sulfonate salt group, and has the sulfonic acid group in a high concentration.

The inventors of the present invention made comprehensive study to offset the above disadvantages, and found that the use of a polymer having sulfonic acid groups and being soluble in water and/or olefin allows the hydration of olefin to proceed effectively with a high yield and the resulting tertiary alcohol can be separated from the catalyst by simple operation.

SUMMARY OF THE INVENTION:

The present invention intends to provide a process for preparing a catalyst having a high activity for producing a tertiary alcohol by hydration of olefin at a high yield at low cost.

The present invention also intends to provide a process for producing a tertiary alcohol by hydration reaction of an olefin by use of the catalyst.

The process for producing the catalyst, a polymer having sulfonic acid groups, of the present invention comprises subjecting a polymer having sulfonate salt groups to ion exchange, the ion exchange being practiced by use of a porous-type strongly acidic cation exchange resin.

The process for producing a tertiary alcohol of the present invention comprises hydration of an olefin by use of the polymer as a catalyst having sulfonic acid groups and being soluble in water and/or olefin.

BRIEF DESCRIPTION OF THE DRAWING:

FIG. 1 is a flowchart of a specific example of practicing the present invention.

DETAILED DESCRIPTION OF THE PREFERRED EMBODIMENT:

The process of the present first invention for producing a polymer having sulfonic acid groups is described below. In the present invention, a polymer having sulfonate salt groups is subjected to ion exchange by use of a porous-type strongly acidic cation exchange resin to derive a polymer having sulfonic acid groups.

The polymer as the starting material of the present invention includes polystyrenesulfonate salts, polynaphthalenesulfonate salts, polyvinylsulfonate salts, stryenesulfonate-maleic anhydride copolymers, and naphthalenesulfonate-formalin copolymers. The polymer having sulfonate salt groups may be substituted partially by a group of alkyl, alkoxy, halo, carboxyl, ester, nitrile, nitro, N-alkylamide, or the like on the backbone of the polymer molecule. Preferred polymer having sulfonate salt groups includes polystyrenesulfonate salt, polyvinylsulfonate salt, and mixtures thereof.

The cation of the sulfonate salt includes lithium, sodium, potassium, cesium, magnesium, calcium, baryllium, aluminum, nickel, copper zinc, cobalt, tellurium, vanadium, titanium, iron, chromium, manganese, ammonium, and silver. Of these cations, sodium and potassium are preferred.

The polymer having sulfonate salt groups as the starting material is usually handled in a state of an aqueous solution. The concentration is preferably in the range of from 10 to 50% by weight since the viscosity of the aqueous solution is high at a higher concentration while condensation operation is required at a lower concentration, although the concentration thereof is not limited specially. If necessary, an organic solvent miscible with the aqueous polymer solution such as an alcohol, a ketone, or an ether may be added to the aqueous polymer solution.

The ion exchange resin used for the preparation of the catalyst in the present invention is a porous-type strongly acidic cation exchange resin which is derived, for example, from a styrene-divinylbenzene copolymer, or the like. An example of the exchange group is a sulfonic acid group. Strongly acidic ion exchange resins are classified into gel type ones and porous-type ones according to the physical state of the pores. The gel type ion exchange resin has only micropores which form fine pores on swelling, while the porous-type ion exchange resin has, in addition to the micropores, macropores which are physical fine pores and exist even in a dry state. The porous-type ion exchange resins include MP type resins (macroporous resin), MR type resins (resins having a macro-reticular structure), and the like (See: Peterotech, Vol. 10, No. 12, page 23 (1987), etc.).

The porous-type strongly acidic cation exchange resin useful in the present invention may be produced by any process. The resin, for example, may be produced by sulfonating with sulfuric acid a particulate styrene-divinylbenzene copolymer as the base resin. The MP type base resin and the MR type base resin are characterized in the solvents used for their production. In a process for producing the MP type base resin, a water-insoluble organic solvent which is capable of dissolving the monomer sufficiently and capable of swelling the formed polymer sufficiently, such as an aromatic hydrocarbon like benzene and toluene, is added to the polymerization system. In a process for producing the MR type base resin, a water-insoluble organic solvent which is capable of dissolving the monomer sufficiently but is incapable of swelling the formed polymer, such as a secondary alcohol, is added to the polymerization system.

The porous-type cation exchange resin useful in the present invention and available commercially is exemplified by Amberlist 15E (made by Japan Organo Co., Ltd.) as the MR type; and Diaion PK220 (makde by Mitsubishi Chemical Industries Ltd.) and Duolite C-264 (made by Sumitomo Chemical Co., Ltd.) as the MP type.

The porous-type strongly acidic ion-exchange resin has many macropores which are physical fine pores and do not disappear in a dry state. With the porous-type strongly acidic ion-exchange resin, presumable, even a high-molecular polymer electrolyte such as a polystrene-sulfonate salt diffuses readily into the interior of the ion-exchange resin through many macropores, thereby the ion-exchange groups in the ion-exchange resin being utilized effectively and the desired ion exchange being practiced with a small amount of the ion-exchange resin in a short time.

The ion-exchange resin used in the present invention is preferably in a spherical form having particle diameter in the range of from about 0.3 to about 1.0 mm.

The method of the ion exchange is not specially limited in the present invention. The ion exchange can be practiced in an ordinary method, including a method in which a porous-type strongly acidic cation exchange resin is added in a required amount directly to a solution of a polymer having sulfonate salt groups and the mixture is stirred for a required time; and a method in which a solution of a polymer having sulfonate salt groups is made to flow in a predetermined amount through a column having an ion-exchange resin packed therein. The ion-exchange is conducted usually at room temperature, but may be conducted at a higher temperature of up to 120° C. If necessary, the ion exchange process is repeated to obtain the polymer having the sulfonic acid group at a high ion-exchange ratio. Thus a solution of a polymer having sulfonic acid groups is obtained as desired.

The polymer having sulfonic acid groups as the catalyst may have remaining sulfonate salt groups partially. The remaining ratio of the sulfonate salt groups in the catalyst polymer having sulfonic acid groups is preferably not higher than 80%. At the higher ratio, undesirably the catalytic activity for olefin hydration falls significantly.

The porous-type strongly acidic cation-exchange reins, after use, can readily be regenerated in a usual manner, for example, by flowing aqueous hydrochloric acid or sulfuric acid solution through the resin for repeated use.

The hydration reaction of olefin which is the present second invention is described below. In this reaction, the polymer having sulfonic acid groups (hereinafter referred to as "sulfonic acid-containing polymer") which has been prepared according to the present first invention is useful as the catalyst. However, a sulfonic acid-containing polymer prepared by any other method is also useful. For example, a sulfonic acid-containing polymer may be prepared by a conventional polymerizing or copolymerizing process to obtain a polymer having sulfonate salt groups and subsequently changing the polymer to a sulfonic acid-containing polymer by conventional ion exchange, electrophoresis, or a like process. Further after preparation of a polymer having no sulfonic acid group, a sulfonic acid group may be introduced later.

The olefin as the starting material of the present invention includes isobutene, α- methylstyrene, isoprene, and/or mixtures thereof. The olefin may contain a hydrocarbon mixture which is inert to hydration reaction. For example, the isobutene may contain saturated and unsaturated $C_4$ hydrocarbons such as 1-butene, cis-2-butene, trans-2-butene, trans-2-butene, n-butene, and isobutane. The α-methylstyrene may contain an aromatic hydrocarbons such as benzene, toluene, xylene, and cumene. Examples of the olefin source containing a hydrocarbon inert i hydration reaction are a by-product $C_4$ fraction obtained form fluid catalytic cracking of petroleum, a distillation fraction of catalytic dehydrogenation of n-butane, and so called "spent BB" obtained by removing butadiene from $C_4$ fraction of a naphtha cracking product.

The sulfonic acid-containing polymer is required to be soluble in water or the olefin. The polymer has preferably a weight-average molecular weight of from 500 to 5,000,000, more preferably from 1,000 to 1,000,000. The concentration of the sulfonic acid-containing polymer as the catalyst is not specially limited, and may be in the range of from 5% by weight to saturation concentration. The solvent for the polymer is preferably water which is also the reaction medium. If necessary, a solvent like dioxane and acetone which is inert to the sulfonic acid-containing polymer, olefin, and water may be added. Furthermore, tertiary alcohol which is a reaction product may be added thereto without any disadvantage.

The reaction temperature is not specially limited but is preferably in the range of from 10° to 120° C., more preferably from 30° to 100 C. At a temperature higher than 120° C., the conversion ratio of the olefin at equilibrium of hydration reaction is remarkably low to give extremely low yield of the tertiary alcohol, while at a temperature lower than 30° C., the reaction rate is low to give low yield of the tertiary alcohol.

The reaction pressure in the present invention is in the range of from ordinary pressure to 30 kg/cm$^2$. The olefin may be fed in a gas state or liquid state to the reaction system. In consideration of the hydration reaction rate of the olefin, preferably the reaction pressure is made sufficiently high to allow the olefin to be in a liquid state. The reaction pressure may be controlled by addition of an inert gas such as nitrogen, argon, and carbon dioxide, if necessary.

The reaction of the present invention may be conducted in any type of reactor, such as a stirred tank reactor, an external circulation type reactor, a tower type reactor, and a tubular reactor. The reaction may be conducted in a batch system, a semi-batch system, or a continuous system. A counter-current multi-stage continuous operation is preferred in consideration of high conversion of the olefin, and high purity and high productivity of the intended tertiary alcohol.

According to the present invention, an olefin is hydrated in the presence of a sulfonic acid-containing polymer to give a tertiary alcohol. The resulting tertiary alcohol is separated from the catalyst. The separation may be conducted by filtration by means of a separation membrane because the catalyst is a polymer soluble in water or in a hydrocarbon mixture. The separation of the catalyst by filtration prior to distillation enables distillation purification of the product under ordinary pressure without decrease of the product yield caused by dehydration or a side reaction of the tertiary alcohol, whereby energy consumption required in vacuum distillation is reduced and the cost is reduced. The filtration for the separation includes microfiltration, ultrafiltration, reverse osmosis, and so forth. However, in the present invention, the filtration separation of the catalyst is not necessarily required. The tertiary alcohol may be separated, for example, by distillation under reduced pressure.

In the present invention, as a sulfonic acid group soluble in water and/or olefin is used as the catalyst, the reaction mixture after the hydration reaction separates, if left standing, is subjected to a two-phase separation, thus separating into a phase containing the catalyst and a phase containing no catalyst. The two-phase separation, is conducted at a temperature in the range of from 0° to 130° C., preferably from 20° to 100° C. If the amount of the tertiary alcohol thus produced is large, the two-phase separation is easily performed at room temperatures. If the two-phase separation is hardly performed, the mixture may be heated to a temperature of 60° C. or higher or in some cases 80° C. or higher. The pressure for the phase separation is not specially limited, but the separation is preferably conducted under the same pressure as in the olefin hydration reaction for convenience of process design. The phase containing no catalyst is separated form the phase containing the catalyst by a decanter or a like means. The tertiary alcohol is readily purified from the phase containing no catalyst by an ordinary method such as distillation. The aqueous phase continuing the catalyst is recycled, without treatment, as the aqueous catalyst solution. In the two-phase separation, a suitable inert solvent may be added to the reaction system. The inert solvent includes butanes, pentanes, hexanes, cyclohexane, benzene, toluene, xylene, and alcohols.

The process of the present invention is described specifically by reference to the drawing. An olefin, the starting material, is introduced into a reactor 1 through a line 4. An aqueous catalyst solution separated by a decanter 2 to be recycled (line 7) and a replenished aqueous catalyst solution (line 3) are combined and introduced to the reactor 1. The reaction is conducted in a counter current manner. The reaction mixture after the reaction is discharged through a line 5 and introduced to the decanter 2, where the reaction mixture is separated into an aqueous phase containing the catalyst and an organic phase containing the tertiary alcohol. The organic phase containing the tertiary alcohol is sent through a line 8 to a purification column such as a distillation column. The aqueous phase separated by the decanter 2 is recycled through the line 7 to the reactor 1. The remaining hydrocarbon is removed from a line 6.

The separation of the tertiary alcohol from the catalyst by the two-phase separation or filtration gives advantages below:

(1) Decrease of the yield by dehydration or other side reaction is not caused since the layer containing the tertiary alcohol obtained by two-phase separation or filtration does not contain catalyst.

(2) Distillation purification of the tertiary alcohol is feasible under an ordinary pressure instead of vacuum distillation conducted in a conventional process, since the tertiary alcohol is separated prior to the distillation from the aqueous layer containing the catalyst. Further the amount to be processed in the distillation step is remarkably reduced, hence enabling minimized the distillation plant.

(3) The catalyst is less liable to be deteriorated by heat and the catalyst layer can be recycled without treatment, since the catalyst layer is separated from the reaction mixture prior to distillation.

The catalyst may be separated from the produced tertiary alcohol by filtration with a separation membrane since the catalyst is a water-soluble polymer. Thereby the same separation effect as in the above two-phase separation can be achieved. The filtration method includes micro-filtration, ultrafiltration, and reverse osmosis.

According to the present invention, a tertiary alcohol is produced by hydration of olefin with high yield at low cost, and the catalyst employed in the hydration assures a high ion-exchange ration of the sufonicate salt to the sulfonic acid group and a very high quality.

The present invention is described in more detail without limiting the invention in any way.
catalyst preparation

EXAMPLES 1–4

200 Grams of aqueous solutions of sodium polystyrene-sulfonate (resin content: 20% by weight) each having a different molecular weight were respectively mixed with 130 g (dry weight) of Amberlist 15E (made by Japan Organo Co., Ltd.), and the mixture was stirred for one hour. Then the Amberlist 15E was removed by filtration. Sodium in the filtrate was determined and the ion exchange ratio of the polystyrenesulfonic acid was derived therefrom. The results are shown in Table 1.

Ion exchange ratio (%) =

100 − ((sodium sulfonate)/ (sulfonic acid group in filtrate + sodium sulfonate group in filtrate)) × 100

EXAMPLES 5 AND 6

200 Grams of aqueous solutions of sodium polystyrenesulfonate (resin content: 20% by weight) each having a different molecular weight were respectively mixed with 100 g (dry weight) of Amberlist 15E (made by Japan Organo Co., Ltd.), and the mixture was stirred for one hours. The amberlist 15E was removed by filtration. Then the filtrate was gain treated for ion exchange by use of 50 g of Amberlist 15E. The ion exchange ratios of the resulting aqueous polystyrenesulfonic acid solutions are shown in Table 1.

Comparative Example 1

The ion exchange reaction was conducted in the same manner as in Example 1 except that the the ion-exchange resin was replaced by Amberlite IR-120 (gel type cation-exchange resin, make by Japan Organo Co., Ltd.) and the ion-exchange reaction was conducted for 24 hours. The ion exchange ratio is shown in Table 1.

TABLE 1

|  | Molecular weight of acid | Ion exchange ratio (%) |
| --- | --- | --- |
| Example 1 | 10,000 to 30,000 | 94 |
| Example 2 | 50,000 to 100,000 | 95 |
| Example 3 | 400,000 to 600,000 | 92 |
| Example 4 | 800,000 to 1,200,000 | 90 |
| Example 5 | 10,000 to 30,000 | 100 |
| Example 6 | 50,000 to 100,000 | 99 |
| Comparitive example 1 | 10,000 to 30,000 | 3 |

EXAMPLES 7 TO 10

Catalysts were prepared in the same manner as in Example 1 except that the kind of the polymer and the amount of the ion-exchange resin were changed as shown in Table 2. As clearly understood from Table 1 when a porous-type, strongly acidic cation exchange resin is used, it is possible to obtain the polystyrene sulfonic acid at a higher ion-exchange ratio in a shorter time and with a smaller amount of resin irrespective of the degree of the molecular weight the polystyrene sulfonate salt as compared with when a gel-type cation exchange resin is used, and further it is possible to achieve a still higher ion-exchange ratio by repeating he ion-exchange.

Hydration Reaction of Isobutene

The reaction products were analyzed by neutralizing the sample wit sodium hydroxide and subjecting it to gas chromatographic analysis by use of dimethoxyethane as the internal standard.

Hereinafter in Examples, tertiary butyl alcohol is referred to as TBA.

EXAMPLES 11 TO 13

Into an autoclave, there were placed 5 g of isobutene, and 150 ml of 10% by weight solution of a polystyrenesulfonic acid in water. The autoclave was closed tightly and the reaction was allowed to proceed with stirring at 70° C. for 2 hours. The results were as shown in Table 3.

In examples 11 to 13, the selectivity of TBA was 100% without a detectable by-product such as diisobutene, and triisobutene.

TABLE 3

|  | Molecular weight of polymer | Ion-exchange ratio of sulfonate group (%) | Conversion ratio of isobutene (%) |
| --- | --- | --- | --- |
| Example 11 | 10,000 | 80.0 | 94 |
| Example 12 | 10,000 | 63.5 | 93 |
| Example 13 | 50,000 | 75.3 | 90 |

EXAMPLE 14

The reaction was conducted in the same manner as in Example 11 except that the isobutene as the starting material was changed to 16.8 g of a spent $C_4$ fraction (having a composition shown in Table 5, containing 5 g of isobutene). The by-product, diisobutene and secondary butanol, were not detected. TBA was obtained with the selectivity of 100% at isobutene conversion ratio of 80%.

EXAMPLE 15

10 Grams of isobutene was allowed to react by use of 50 ml of polystyrenesulfonic acid having a hydrogen ion concentration of 0.2 N (molecular weight: 10,000, exchange ratio of sodium in sulfonate group: 63.5%) as the catalyst at 60° C. for 30 minutes. The rate of formation of TBA per gram of the catalyst was 0.470 g/hr.g-catalyst.

Comparative Example 2

The reaction was conducted in the same manner as in Example 15 except that the catalyst was changed to an aqueous silicotungstic acid solution having a hydrogen ion concentration of 0.2 N. The rate of formation of TBA per gram of the catalyst was 0.253 g/hr.g-catalyst.

EXAMPLE 16

The catalyst obtained in Example 7 was concentrated to a concentration of 1.2 N in terms of hydrogen ion. 20 g of this concentrated aqueous solution and 5 g of isobutene as the starting material were placed in an autoclave, and the reaction was allowed to proceed at 70° C. for 3 hours. After the reaction, pressure in the autoclave was brought to ordinary pressure, and unreacted isobutene was purged. The reaction solution was transferred to a separatory funnel, and allowed to separate at 25° C. into two layers. The upper layer and the lower layer were respectively analyzed to determine the isobutene conversion ratio and the TBA partition ratio. The results are shown in Table 4. The selectivity of TBA was 100% without a detectale by-product such as diisobutene and triisobutene.

EXAMPLES 17 AND 18

The reaction was conducted in the same manner as in Example 16 except that isobutene as the starting material was used in an amount of 10 g, and 20 g, respectively. The results of two-phase separation at 25° C. after purge of unreacted isobutene after the reaction are shown in Table 4. In both of Example 17 and 18, TBA was obtained at a selectivity of 100% without a detectable by-product such as diisobutene and triisobutene.

EXAMPLES 19 AND 20

The catalyst obtained in Example 8 was concentrated to a concentration of 1.2 N in terms of hydrogen ion. 20 g of this concentrated aqueous solution, and 5 g and 10 g, respectively, of isobutene as the starting material were placed in an autoclave, and the reaction was allowed to proceed at 70° C. for 3 hours. The results of two-phase separation at 25° C. after purge of unreacted isobutene after the reaction are shown in Table 4. In both of Examples 19 and 20, TBA was obtained at a selectivity of 100% without a detectable by-product such as diisobutene and triisobutene.

EXAMPLE 21

The catalyst obtained in Example 1 was concentrated to a concentration of 1.2 N in terms of hydrogen ion. 20 g of this concentrated aqueous solution and 10 g of isobutene were placed in an autoclave, and the reaction was allowed to proceed at 70° C. for 3 hours. The results of two-phase separation at 82° C. after purge of unreacted isobutene after the reaction are shown in Table 4. TBA was obtained at a selectivity of 100% without a detectable by-product such as diisobutene and triisobutene.

EXAMPLE 22

The reaction was conducted in the same manner a in Example 16 except that the isobutene as the starting material was changed to 16.8 g of a spent BB fraction (having a composition shown in Table 5, containing 5 g of isobutene). The results of two-phase separation at 25° C. after purge of unreacted spent BB after the reaction are shown in Table 4. TBA was obtained at a selectivity of 100% without detection of by-products such as diisobutene and secondary butanol.

EXAMPLE 23

The reaction was allowed to proceed in the same manner as in Example 17, except that the catalyst was changed to the one obtained in Example 9. The results of two-phase separation at 25° C. after purge of unreacted isobutene after the reaction are shown in Table 4. TBA was obtained at a selectivity of 100% without detection of by-products such as diisobutene and secondary triisobutene.

EXAMPLE 24

The reaction was allowed to proceed in the same manner as in Example 17, except that the catalyst was changed to the one obtained in Example 10. The results of two-phase separation at 25° C. after purge of unreacted isobutene after the reaction are shown in Table 4. TBA was obtained at a selectivity of 100% without a detectable by-product such as diisobutene and secondary triisobutene.

Comparative Examples 3 and 4

The reaction was allowed to proceed in the same manner as in Example 1 except that the catalyst was changed respectively to silicotungstic acid, and p-toluenesulfonic acid, each having a concentration of 1.2 N in terms of hydrogen ion. The reaction mixture after the reaction was a homogeneous solution. This homogeneous solution did not separate into two layers even when the temperature was raised to 90° C., or sodium was added as a cation. The results of analysis of the homogeneous solution are shown in Table 4. The selectivity of TBA was 100% without a detectable by-product such as diisobutene and triisobutene.

TABLE 2

|  | Polymer | Molecular weight | Concentration (%) | Amount of ion-exchange resin (g) | Ratio of exchange (%) |
|---|---|---|---|---|---|
| Example 7 | Sodium polystyrenesulfonate | 10,000 | 20 | 50 | 65 |
| Example 8 | Sodium polystyrenesulfonate | 10,000 | 20 | 20 | 34 |
| Example 9 | Sodium polyvinylsulfonate | — | 25 | 200 | 39 |
| Example 10 | Sodium polystyrenesulfonate | 50,000 | 20 | 50 | 63 |

TABLE 4

|  | Catalyst | Charged isobutene (g) | Reaction ratio of isobutene (%) | Partition ratio of TBA (%) Upper layer | Partition ratio of TBA (%) Lower layer |
|---|---|---|---|---|---|
| Example 16 | Example 7 | 5 | 85 | 15 | 85 |
| Example 17 | Example 7 | 10 | 83 | 67 | 33 |
| Example 18 | Example 7 | 20 | 68 | 83 | 17 |
| Example 19 | Example 8 | 5 | 77 | 31 | 69 |
| Example 20 | Example 8 | 10 | 66 | 75 | 25 |
| Example 21 | Example 1 | 10 | 95 | 60 | 40 |
| Example 22 | Example 7 | 5 | 42 | 26 | 74 |
| Example 23 | Example 9 | 10 | 47 | 89 | 11 |
| Example 24 | Example 10 | 10 | 73 | 66 | 34 |
| Comparative example 3 | Silicotungstic acid | 10 | 93 | 0 | 100 |
| Comparative example 4 | p-Toluene-sulfonic acid | 10 | 87 | 0 | 100 |

TABLE 5

| Hydrocarbon | Content (volume %) |
|---|---|
| Isobutene | 29.2 |
| 1-Butene | 21.4 |
| 2-Butene | 17.2 |
| Butane | 22.8 |
| Propane | 7.3 |
| Butadiene | 1.5 |

What is claimed is:

1. A process for preparing a tertiary alcohol comprising hydrating an olefin in the presence of polystyrenesulfonic acid or polyvinylsulfonic acid as a catalyst in liquid form which is soluble in water or the olefin.

2. The process of claim 1 wherein the olefin is isobutene and the tertiary alcohol is tertiary butanol.

3. The process of claim 1 wherein the olefin is hydrated continuously in a counter-current reactor.

4. A homogeneous process for preparing a tertiary alcohol comprising the steps of:

(1) hydrating an olefin selected for the group consisting of isobutene, α-methylstyrene, isoprene or mixtures thereof in an aqueous solution, optionally in the presence of an inert solvent, at a temperature of from 30° to 120° C. and at a pressure from atmospheric up to 30 kg/cm$^2$ in the presence of polystyrene sulfonic acid or polyvinylsulfonic acid as a catalyst soluble in the aqueous solution, the olefin or both, and thereafter (2) separating the catalyst in liquid form and from the so produced tertiary alcohol.

5. The process of claim 4 wherein following hydration the reaction mixture is separated into one phase containing the liquid catalyst and another phase containing no catalyst.

6. The process of claim 4 wherein the reaction solution following hydration is separated by filtration into the tertiary alcohol and an aqueous catalyst solution.

7. The process of claim 4 wherein the aqueous solution also contains an inert solvent selected from the group consisting of butanes, pentanes, hexanes, cyclohexane, benzne, toluene, xylene and alcohols.

* * * * *